United States Patent [19]

Schrock

[11] 3,988,332

[45] Oct. 26, 1976

[54] HYDROCARBYLIDENE COMPOUNDS OF NIOBIUM AND TANTALUM

[75] Inventor: Richard Royce Schrock, Wilmington, Del.

[73] Assignee: E. I. Du Pont de Nemours and Company, Wilmington, Del.

[22] Filed: Apr. 21, 1975

[21] Appl. No.: 570,259

Related U.S. Application Data

[63] Continuation-in-part of Ser. No. 471,810, May 20, 1974, abandoned.

[52] U.S. Cl............................... 260/429 R; 427/166; 252/431 R; 260/242; 260/340.6; 260/346.1 M; 260/348.5 R; 260/614 A; 260/677 H; 260/682; 260/683 R; 260/15
[51] Int. Cl.².......................................... C07F 9/00
[58] Field of Search .............................. 260/429 R

[56] References Cited
UNITED STATES PATENTS

3,396,184   8/1968   Juvinall............................ 260/429 R 3,763,197   10/1973   Collier et al. ............... 260/429 R X

OTHER PUBLICATIONS

Wailes, J. Organometallic Chem. vol. 75, pp. 325–334, (1974).
Chem. Abstracts, vol. 78, 159789w (1973).
Chem. Abstracts, vol. 80, 60013t (1974).
Mowat et al., J. Chem. Soc. p. 1120 (1973).
Juvinall, J.A.C.S. vol. 86, 4202 (1964).

*Primary Examiner*—Helen M. S. Sneed
*Attorney, Agent, or Firm*—Anthony P. Mentis

[57] ABSTRACT

Certain hydrocarbylidene compounds of niobium and tantalum react with oxo compounds to form olefins and are also useful as oxygen scavengers. The compounds can also be used to deposit tantalum or niobium mirrors by thermal decomposition. Exemplary is trineopentyl(neopentylidene)tantalum of the formula

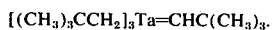

10 Claims, No Drawings

HYDROCARBYLIDENE COMPOUNDS OF NIOBIUM AND TANTALUM

RELATED APPLICATION

This application is a continuation-in-part of my application Ser. No. 471,810 filed May 20, 1974, now abandoned.

BACKGROUND OF THE INVENTION

1. Field of the Invention

This invention relates to novel organic compounds of niobium and tantalum.

2. The Prior Art

Mowat and Wilkinson, J. Chem. Soc. Dalton, 1120 (1973) have described the preparation of trineopentyltantalum dichloride. It was noted that the addition of $TaCl_5$ to an excess of neopentyl Grignard reagent produced "a dark brown oil containing many species," but no particular compound was described or isolated.

SUMMARY OF THE INVENTION

The compounds of the present invention have the general formula $$Cp_aL_bQ_cM=CR^1R^2$$
$$|$$
$$X$$
$$\text{I}$$

wherein

Cp is a π-cyclopentadienyl group having up to one alkyl substituent;

L is a monophosphine of the formula $P(R^3)_3$ or a diphosphine of the formula $(R^3)_2PCH_2CH_2P(R^3)_2$ in which $R^3$ is alkyl or aryl;

Q is alkyl, aralkyl or diarylmethyl in which the β-carbon is not bonded to hydrogen;

M is niobium or tantalum;

X is F, Cl, Br, I, or alkyl, aralkyl or diarylmethyl in which the β-carbon is not bonded to hydrogen;

$R^1$ and $R^2$ individually are hydrogen, tertiary alkyl or aryl;

alkyl has 1–10 carbons, aralkyl has 7–10 carbons and aryl, including the aryl groups in diarylmethyl, has 6–10 carbons;

a, b and c individually are 0, 1 or 2; with the proviso that b is 1 when L is a diphosphine; or 2 when L is a monophosphine; and with the further provisos that when a is 2, b and c are each 0;

when a is 1, b is 1 or 2, c is 1, Q and X are each $CH_3$ and $R^1$ and $R^2$ are each H; and when a is 0, b is 0, c is 2 and X is the same as Q.

Examples of alkyl groups that can be substituents in the cyclopentadienyl ring are methyl, ethyl, isopropyl, t-butyl, hexyl, octyl and decyl. Because of the commercial availability of cyclopentadiene and methylcyclopentadiene, the cyclopentadienyl, and methylcyclopentadienyl groups are preferred. Examples of suitable groups are thus cyclopentadienyl, methylcyclopentadienyl, ethylcyclopentadienyl, isopropylcyclopentadienyl, t-butylcyclopentadienyl, hexylcyclopentadienyl, octylcyclopentadienyl and decylcyclopentadienyl.

Examples where L is a monophosphine are trimethylphosphine, triisobutylphosphine, trioctylphosphine, tridecylphosphine, triphenylphosphine, tritolylphosphine, and trinaphthylphosphine.

Examples where L is a diphosphine are ethylenebis(dimethylphosphine), ethylenebis(diethylphosphine), ethylenebis(dihexylphosphine), ethylenebis(diphenylphosphine), ethylenebis[di(2,3,5,6-tetramethylphenyl)phosphine], and ethylenebis(dinaphthylphosphine). Preferably the alkyl groups in both the monophosphines and the diphosphines contain from 1–4 carbons and most preferably they are methyl.

Examples of Q are methyl, neopentyl, 2,2,4,4-tetramethyl-3-pentyl, benzyl, p-ethylbenzyl, naphthylmethyl, β,β-dimethylphenethyl ("neophyl"), diphenylmethyl, and ditolylmethyl. A preferred class of Q groups comprises alkyl and aralkyl and most preferably Q is methyl, neopentyl or benzyl.

The $(CH_3)_3CCH_2$ moiety is a neopentyl group, and will frequently be represented hereinafter by the abbreviated formula $C_5H_{11}$.

Examples of X are methyl, neopentyl, 2,2,4,4-tetramethyl-3-methyl, benzyl, p-ethylbenzyl, naphthylmethyl, β,β-dimethylphenethyl ("neophyl"), diphenylmethyl, and ditolylmethyl. The preferred values of X are Cl, Br, methyl, neopentyl, benzyl, and diphenylmethyl.

Preferred values of $R^1$ and $R^2$ are hydrogen, aryl and t-butyl. Most preferably $R^1$ is hydrogen and $R^2$ is hydrogen, t-butyl, or phenyl that is, only one of the R groups is a tertiary alkyl group.

The terms "aryl" and "ar" are employed here to denote a radical derived from a hydrocarbon, having as its only unsaturation aromatic unsaturation in six membered carbocyclic rings, by removal of a hydrogen atom from a nuclear carbon atom of an aromatic ring. Examples of aryl groups are phenyl, 1- and 2-naphthyl, o-, m- and p-tolyl, ethylphenyl, butylphenyl, xylyl, and trimethylphenyl.

Three methods can be used to prepare the products of the invention corresponding to the formula $$Q_2M=CR^1R^2$$
$$|$$
$$X$$

where $a = b = o$. Since in these compounds Q is the same as X, they can be formulated alternatively as $Q_3M=CR^1R^2$.

In the first method, a trihydrocarbylmetal dichloride, $Q_3MCl_2$, such as trineopentyltantalum dichloride or trineopentylniobium dichloride is reacted with two moles of a hydrocarbyllithium compound in which the hydrocarbyl group corresponds to the hydrocarbylidene group in the product:

$$(C_5H_{11})_3MCl_2 + 2LiCHR^1R^2 \rightarrow (C_5H_{11})_3M=CR^1R^2 + CH_2R^1R^2 + 2LiCl \quad (1)$$

In the second method, four moles of a hydrocarbyllithium, QLi, such as neopentyllithium are reacted with one mole of a hydrocarbyltantalum tetrachloride or hydrocarbylniobium tetrachloride in which the hydrocarbyl group corresponds to the hydrocarbylidene group in the product:

$$4C_5H_{11}Li + Cl_4MCHR^1R^2 \rightarrow (C_5H_{11})_3M=CR^1R^2 + C_5H_{12} + 4LiCl \quad (2)$$

The ultimate source of tantalum or niobium in each of these three processes is tantalum pentachloride or nioniobium pentachloride. In the third method, a trihydrocarbyl (hydrocarbyliden)tantalum compound such as trineopentyl(neopentylidene)tantalum, the compound of formula I in which $R^1$ is t-butyl and $R^2$ is hydrogen, is prepared directly from $TaCl_5$ by reacting it with five moles of an appropriate hydrocarbyl Grignard reagent such as neopentylmagnesium chloride:

$$TaCl_5 + 5C_5H_{11}MgCl \rightarrow (C_5H_{11})_3Ta=CHC(CH_3)_3 \\ + 5MgCl_2 + C_5H_{12} \quad (3)$$

The corresponding niobium compounds can be similarly prepared from $NbCl_5$.

Products of the invention in which X is Cl or Br can be prepared by reacting the appropriate dihydrocarbylmetal trihalide with two moles of cyclopentadienylthallium:

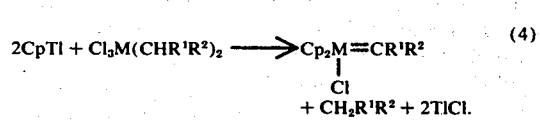

$$+ CH_2R^1R^2 + 2TlCl.$$

Products in which X is F or I can be made by conventional halide-exchange techniques. The halide exchange can be carried out on the first product of equation (4) or on the dihydrocarbylmetal trichloride or tribromide.

Products in which X is hydrocarbyl can be made by reacting the appropriate hydrocarbyllithium, or preferably a diamine complex thereof, with the product of equation (4). For example:

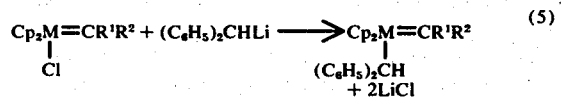

This method can be used for products in which the X and $CHR^1R^2$ hydrocarbyl groups are either the same or different. When they are the same, the products can also be made by reacting the appropriate trihydrocarbylmetal dichloride with two moles of cyclopentadienylthallium:

When $R^1R^2CH$ is methyl, the intermediate $Cp_2M(CH_3)_3$ does not eliminate $R^1R^2CH_2$, methane, spontaneously to give the desired product. The latter is obtained by demethylating $Cp_2M(CH_3)_3$ to a cationic species with triphenylmethonium tertrafluoroborate and deprotonating the cation with a base such as trimethyl(methylene)phosphorane:

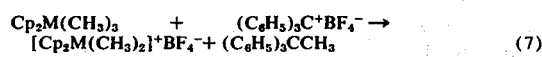

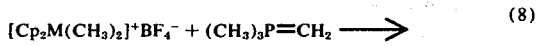

-continued

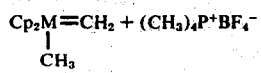

Correspondingly, the products of the formula

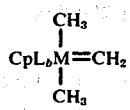

where a is 1, are made by reacting $CpM(CH_3)_4$ with triphenylmethonium tetrafluoroborate, reacting the product with L, and then deprotonating with a suitable base:

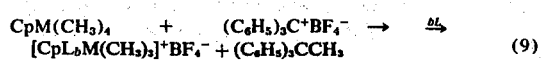

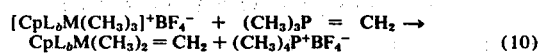

These compounds are of the formula $Cp_aQ_cM(X)=CR^1R^2$, where $a$ is 0 or 2, $c$ is 0 or 2, X is alkyl, aralkyl, or aryl, all as defined previously. Under the terms of the provisos given earlier it will be seen that such compounds can alternatively be formulated as $Cp_aQ_dM=CR^1R^2$, where $a$ is 0 or 2, $d$ is 1 or 3, and $a + d$ is 3.

Some products of the invention react with molecular oxygen and certain organic compounds containing carbonyl groups to give useful ethylenically unsaturated compounds. Examples of such compounds containing carbonyl groups are aldehydes, ketones, carboxylic esters, and carboxamides. In addition to its preparative value, this reaction is useful as a diagnostic tool to show the presence of products of the invention in a reaction mixture. The reactions with oxygen and with oxo compounds can be represented generically as follows:

$$2Cp_aQ_dM=CR^1R^2+O_2 \rightarrow R^1R^2C=CR^1R^2 \qquad a$$

The fate of the $Cp_aQ_dM$ moiety is not known with certainty.

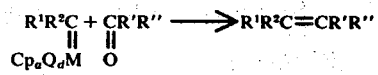

R' and R" represent the organic moieties of the oxo compound and are described in more detail later. Again, the fate of the $Cp_aQ_dM$ grouping is not known with certainty.

SPECIFIC EMBODIMENTS OF THE INVENTION

This invention is further illustrated by the following examples, which should not, however, be construed as fully delineating the scope of this discovery.

In order to avoid the presence of oxygen and moisture, all experiments below were carried out in an atmosphere of dry nitrogen.

Trineopentyltantalum dichloride was prepared by the method of Mowat and Wilkinson, J. Chem. Soc. Dalton, 1120 (1973).

Trimethyltantalum dichloride was prepared by the method of Juvinall, J. Am. Chem. Soc., 86, 4202 (1964).

Dineopentyltantalum trichloride, $(C_5H_{11})_2TaCl_3$, was prepared by the reaction of tantalum pentachloride with an equimolar amount of dineopentylzinc in toluene.

Tribenzyltantalum dichloride, $(C_6H_5CH_2)_3TaCl_2$, was prepared from one mole of tantalum pentachloride and 1.5 moles of dibenzylzinc in toluene.

Trineopentylniobium dichloride, $(C_5H_{11})_3NbCl_2$, was prepared by reaction of niobium pentachloride and an equimolar amount of the monodioxanate of dineopentylmagnesium, $(C_5H_{11})_2Mg(dioxane)$, in ethyl ether.

EXAMPLE 1

Trineopentyl(neopentylidene)tantalum

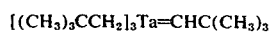
$[(CH_3)_3CCH_2]_3Ta=CHC(CH_3)_3$

A. A solution of 0.5 g of trineopentyltantalum dichloride and 0.17 g of neopentyllithium in 4 ml of pentane was allowed to stand at room temperature for 24 hr in a glass vessel wrapped in foil. (In later experiments it was found that the foil wrapping was unnecessary.) The lithium chloride that had precipitated was separated by filtration, and the filtrate was allowed to stand for another 24 hr at room temperature. No more solid precipitated during this time. Volatile materials were removed under reduced pressure to give trineopentyl(-neopentylidene)tantalum, $(C_5H_{11})_3Ta=C_5H_{10}$, as an orange crystalline solid.

An $^1H$ nmr of the product in $C_6D_6$ showed four singlets in the ratio 1:27:6:9 at τ8.09 (1), τ8.57 (9), τ8.85 (27), and τ9.16 (6).

B. The foregoing procedure was essentially repeated (24-hr reaction period) with double quantities of materials to give 0.85 g (85%) of $(C_5H_{11})_3Ta=C_5H_{10}$. The product was combined with the product from part A, and the mixture was heated in a sublimation apparatus at 80°C/0.5μ. The crystals thus obtained on the cold finger had the same appearance and the same $^1H$ nmr as the original product. A mass spectrum showed a peak at m/e 464.

C. A solution of 5.15 g of $(C_5H_{11})_3TaCl_2$ and 1.75 g of $C_5H_{11}Li$ in 50 ml of pentane was allowed to stand at room temperature for eight hours, and the lithium chloride that precipitated was removed by filtration. When the volume of the filtrate was reduced to about 5 ml under reduced pressure without heating, orange crystals precipitated; they redissolved when the mixture was allowed to warm to room temperature. The mixture was filtered, and the filtrate was kept overnight at −30° C. No crystals appeared. The volume of the solution was reduced from 6 ml to 4 ml, and the solution was allowed to stand overnight again at −30° C. The orange crystals of $(C_5H_{11})_3Ta=C_5H_{10}$ that appeared were separated by filtration; yield 2.5 g. Removal of the rest of the solvent under reduced pressure gave an additional 1.8 g of product. The total yield was 84%.

Anal. calcd. for $C_{20}H_{43}Ta$: C, 51.72; H, 9.33; Ta, 38.95; mol wt, 464; Found: C, 51.39; H, 9.31; Ta, 41.22; mol wt, 472; C, 51.09; H, 9.24; Ta, 42.77; C, 50.86; H, 9.22; (cryoscopic in benzene).

EXAMPLE 2

Trineopentyl(neopentylidene)tantalum

$[(CH_3)_3CCH_2]_3Ta=CHC(CH_3)_3$

A mixture containing the Grignard reagent prepared from magnesium metal and 160 g of neopentyl chloride in about one liter of ethyl ether was added rapidly with stirring to 107 g of tantalum pentachloride and about one liter of ethyl ether. The mixture was stirred for one hour and filtered, and all volatile material was removed from the filtrate under reduced pressure. The residue was extracted with about 200 ml of pentane, and the filtered extract was evaporated under reduced pressure. The residue was volatilized in a sublimation apparatus at 100° C/1μ to give a total of 75 g (50%; 3 crops) of $(C_5H_{11})_3Ta=C_5H_{10}$ as deep-orange nugget-like crystals; mp 71° C (sealed tube).

EXAMPLE 3

Trineopentyl(benzylidene)tantalum

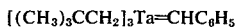
$[(CH_3)_3CCH_2]_3Ta=CHC_6H_5$

A solution of 2.6 g of $(C_5H_{11})_3TaCl_2$ in 100 ml of hexane was cooled to −78° C, and a solution of 2.4 g of benzyl (N,N,',N'-tetramethylethylenediamine)lithium in 30 ml of toluene was added dropwise over one hour with rapid stirring. The mixture was warmed to 25° C, stirred for an additional hour, and filtered, and volatile materials were removed from the deep-orange filtrate under reduced pressure, to give an orange residue that contained trineopentyl(benzylidene)-tantalum.

The presence of the latter was demonstrated by its characteristic reaction with acetone. The residue was taken up in 50 ml of pentane, and 0.4 ml of acetone was added. After 15 min the mixture was filtered, and the filtrate was allowed to stand overnight at room temperature. It was then treated with about 20 ml of 1M HCl. Analysis of the organic portion of the product mixture by gas chromatography and mass spectroscopy showed that 2-methyl-1-phenylpropene had been formed.

If 4-methylbenzyllithium or a suitable diamine complex thereof is used in place of benzyllithium in essentially the procedure of example 3, trineopentyl(4-methylbenzylidene)-tantalum, $(C_5H_{11})_3Ta=CHC_6H_4CH_3$, will be formed. If 1-naphthylmethyllithium or a complex thereof is used, the product will be trineopentyl(1-naphthylmethylene)tantalum, $(C_5H_{11})_3Ta=CHC_{10}H_7$.

EXAMPLE 4

Trineopentyl(methylene)tantalum

$[(CH_3)_3CCH_2]_3Ta=CH_2$

A solution of 1.0 g of trimethyltantalum dichloride and 2.41 g of tantalum pentachloride in 50 ml of toluene was stirred for one hour at room temperature. The resulting solution of methyltantalum tetrachloride was cooled to −78° C, and a solution of 3.15 g of neopentyllithium in 25 ml of ethyl ether was added with stirring over a period of about 20 min. The mixture was warmed to room temperature and filtered, and the solvent was removed from the filtrate under reduced pressure, to give a brown residue that contained trineopentyl(methylene)tantalum, $(C_5H_{11})_3Ta=CH_2$.

The presence of the product was demonstrated by its characteristic reaction with cyclohexanone. The product mixture was dissolved in pentane, 1 ml of cyclohexanone was added, and the mixture was stirred for 5 min. It was then poured into water, and the organic layer was separated and dried over calcium chloride. Methylenecyclohexane was found in the pentane solution by gas chromatography and was identified by mass spectroscopy.

EXAMPLE 5

Trineopentyl(neopentylidene)niobium

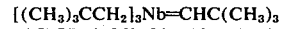

To $(C_5H_{11})_3NbCl_2$ (0.75 g) in 50 ml of pentane at $-78°$ C was added $C_5H_{11}Li$ (0.31 g) in 20 ml of pentane with stirring, and the mixture was allowed to warm to room temperature. The yellow solution turned red as it warmed up, and LiCl precipitated and was filtered off. Pentane was removed in vacuo, to give wine-red, solid $(C_5H_{11})_3Nb=C_5H_{10}$ $^1$H nmr (tol-$d_8$, $\tau$): 7.00 (1, s), 8.59 (9, s), 8.88 (27, s), 9.07 (6, s).

EXAMPLE 6

Chlorodicyclopentadienyl(neopentylidene)tantalum

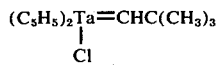

$(C_5H_{11})_2TaCl_3$ (3.0 g) and $C_5H_5Tl$ (3.8 g) were stirred in 25 ml of toluene overnight. A grey solid (3.9 g) was filtered off the next day. The solution volume was decreased to ca. 10 ml and pentane was added to give 1.2 g of yellow, solid $(C_5H_5)_2TaCl=CHC(CH_3)_3$, which was recrystallized from toluene/pentane.

$^1$H nmr ($C_6D_6$, $\tau$): $-0.10$ (1, s), 4.55 (5, s), 4.69 (5, s), 8.70 (9, s); at 60° C the 4.55 and 4.69 coalesced.

$^{13}$C[$^1$H]nmr ($C_6D_6$, ppm from TMS): 273 (CH), 104 ($C_5H_5$), 103 ($C_5H_5$), 34 ($CH_3$).

$(C_5H_5)_2Ta(Br)=CHC(CH_3)_3$ can be made by using $(C_5H_{11})_2TaBr_3$ in place of $(C_5H_{11})_2TaCl_3$ in essentially the process described above. $(C_5H_5)_2Ta(F)=CHC(CH_3)_3$ can be made by reacting either the corresponding chloro or bromo compound with silver fluoride. $(C_5H_5)_2Nb(Cl)=CHC(CH_3)_3$ can be made by substituting $(C_5H_{11})_2NbCl_3$ for $(C_5H_{11})_2TaCl_3$ in essentially the process described above.

EXAMPLE 7

Benzyldicyclopentadienyl(benzylidene)tantalum

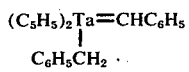

$(C_6H_5CH_2)_3TaCl_2$ (1.05 g) and $C_5H_5Tl$ (1.07 g) were stirred in 25 ml of toluene for one week. The mixture was filtered and the volume reduced to ca. 10 ml. Pentane was added to the filtrate and the solution was held at $-30°$ C for one hour. Filtration gave 0.57 g of crystalline $(C_5H_5)_2Ta(CH_2C_6H_5)=CHC_6H_5$.

$^{13}$C[$^1$H]nmr ($C_6D_6$, ppm from TMS): 246 (CH), 121.4, 123.3, 126.5, 127.1, 127.3, 128.7, 155.2, 157.7 (phenyl carbons), 101.6, 101.0 ($C_5H_5$ carbons), 28.7 ($CH_2$).

Anal. Calcd for $C_{24}H_{23}Ta$: C, 58.55; H, 4.70. Found: C, 57.94; H, 4.76; C, 58.18; H, 4.76.

$^1$H nmr ($C_6D_6$, $\tau$) (different sample prepared by essentially the same method): $-1.03$ (1, s), 2.75 (10, m), 4.93 (10, s), 7.20 (1, d, J = 10), 8.10 (1, d, J = 10).

Correspondingly, dicyclopentadienyl (neopentyl) (neopentylidene)niobium, $(C_5H_5)_2Nb(C_5H_{11})=C_5H_{10}$, can be made from the reaction of $(C_5H_{11})_3NbCl_2$ and $C_5H_5Tl$.

EXAMPLE 8

(Dicyclopentadienyl(diphenylmethyl) (neopentylidene)tantalum

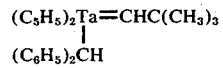

$(C_5H_5)_2Ta(Cl)=CHC(CH_3)_3$ (0.49 g) and $(C_6H_5)_2CHLi\cdot TMEDA$ (0.29 g, TMEDA = N,N,N′,N′-tetramethylethylenediamine) were stirred in 10 ml of toluene for a few minutes, and the mixture was allowed to stand overnight. It was filtered and the toluene was removed from the filtrate in vacuo. The residue was extracted with 25 ml of pentane, and the extract was chilled at $-30°$ C for one hour and filtered, to give 0.28 g of cream-colored $(C_5H_5)_2Ta[CH(C_6H_5)_2]=CHC(CH_3)_3$.

$^1$H nmr ($C_6D_6$, $\tau$): 0.9 (1, s), ca. 2.8 (10, m), 4.96 (10, s), 5.61 (1, s), 8.65 (9, s).

Dicyclopentadienyl(1-naphthylmethyl) (neopentylidene)-niobium, $(C_5H_5)_2Nb(CH_2C_{10}H_7)=C_5H_{10}$, can be prepared by essentially the foregoing method from $(C_5H_5)_2Nb(Cl)=C_5H_{10}$ and the TMEDA complex of 1-naphthylmethyllithium.

EXAMPLE 9

Dicyclopentadienyl(methyl) (methylene)tantalum

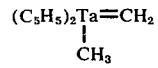

$(C_5H_5)_2Ta(CH_3)_3$ was prepared by stirring a mixture of 10.0 g of $(CH_3)_3TaCl_2$, 18.1 g of $C_5H_5Tl$, and 100 ml of toluene for one hour at room temperature. Thallium chloride was separated by filtration, the volume of the filtrate was reduced to about 25 ml, about 25 ml of pentane was added, and the solution was allowed to stand at $-35°$ C, to give cream-colored crystals in two crops, 6.3 g and 2.0 g; yield 70%.

Anal. Calcd. for $C_{13}H_{19}Ta$: C, 43.84; H, 5.38. Found: C, 43.51; H, 5.37; C, 43.78; H, 5.41; C, 43.66; H, 5.33.

$^1$H nmr ($\tau$, $C_6D_6$): 5.15 (10, s), 9.69 (6, s), 9.79 (3, s).

$[(C_5H_5)_2Ta(CH_3)_2]^+BF_4^-$ was prepared by adding a solution of 3.30 g of $(C_6H_5)_3C^+BF_4^-$ in about 25 ml of dichloromethane to a solution of 3.56 g of $(C_5H_5)_2Ta(CH_3)_3$ in about 25 ml of dichloromethane with stirring. The desired product precipitated as a solid and was separated by filtration; yield 3.8 g (89%). $(C_6H_5)_3CCH_3$, identified by $^1$H nmr, was obtained from the filtrate.

[(C₅H₅)₂Ta(CH₃)₂]⁺BF₄⁻ (0.428 g) in ca. 10 ml of tetrahydrofuran was treated with 0.10 g of (CH₃)₃P=CH₂. All solids dissolved. The solvent was removed in vacuo, and the residue was extracted with 25 ml of toluene, leaving 0.175 g of [(CH₃)₄P]⁺BF₄⁻ (theory 0.198 g). The toluene was removed from the extract in vacuo to give 0.290 g (85%) of crystalline (C₅H₅)₂Ta(CH₃)=CH₂.

¹H nmr (C₆D₆, τ): −0.01 (2, s), 4.91 (10, s), 10.0 (3, s).

Other bases in addition to trimethyl(methylene)-phosphorane that can be used for the deprotonation reaction involved in this preparation include bis(trimethylsilyl)aminolithium and t-butyllithium. Three samples of the product, prepared with these three bases, were combined. The composite was recrystallized for further analysis by dissolving it in the minimum amount of toluene, treating with activated charcoal, filtering, diluting the filtrate with pentane, and cooling at −30° C, to give dicyclopentadienyl(methyl)(methylene)tantalum in the form of shimmering greenish needles.

¹³C[¹H]nrm (C₆D₆, ppm from TMS): 230 (CH₂), 100 (C₅H₅ carbons), −3.8 (CH₃).

Anal. Calcd. for C₁₂H₁₅Ta: C, 42.37; H, 4.44. Found: C, 41.98; H, 4.50; C, 42.10; H, 4.44; H, 4.49.

A single-crystal x-ray study confirmed this compound's structure.

EXAMPLE 10

Dicyclopentadienyl(methyl) (methylene)niobium

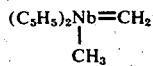

(C₅H₅)₂Nb(CH₃)₃ was prepared by stirring a mixture of 0.42 g of (CH₃)₃NbCl₂, 1.08 g of C₅H₅Tl, and about 20 ml of toluene for one hour at room temperature. TlCl was separated by filtration, the filtrate was evaporated in vacuo nearly to dryness, the residue was triturated with pentane, and the mixture was filtered to give 0.28 g of greenish crystals.

¹H nmr (τ, C₆D₆): ~5.3 (10, s), ~9.7 (6, s), ~9.8 (3, s).

[(C₅H₅)₂Nb(CH₃)₂]⁺BF₄⁻ was prepared by mixing dichloromethane solutions of 0.34 g of (C₅H₅)₂Nb(CH₃)₃ and 0.42 g of (C₆H₅)₃C⁺BF₄⁻, whereupon the product precipitated as a yellow solid; yield 0.31 g. (C₆H₅)₃CCH₃ was identified in the residue from the filtrate.

¹H nmr (τ. CD₃CN): 3.92 (10, s), 9.23 (6, s).

[(C₅H₅)₂Nb(CH₃)₂]⁺BF₄⁻ (0.31 g) in ca. 10 ml of tetrahydrofuran was treated with 0.08 g of (CH₃)₃P=CH₂. Workup as in Example 9, but with extraction by pentane, gave a pentane solution of thermally unstable (C₅H₅)₂Nb(CH₃)=CH₂.

EXAMPLE 11

1,2-Bis(dimethylphosphino)ethane(π-cyclopentadienyl)(dimethyl)(methylene)tantalum

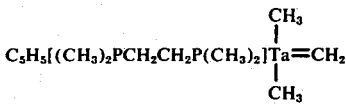

C₅H₅Ta(CH₃)₄ was prepared as follows: C₅H₅Tl (5.0 g) was added slowly with stirring to a solution of 5.0 g of (CH₃)₃TaCl₂ in 20 ml of toluene. The mixture was filterd to remove thallium chloride, and the filtrate was evaporated under reduced pressure to give 5.0 g of C₅H₅Ta(CH₃)₃Cl.

¹H nmr (τ, C₆D₆): 4.45 (5, s), 8.87 (9, s).

A solution of 2.0 g of C₅H₅Ta(CH₃)₃Cl in about 30 ml of ethyl ether was cooled to −78° C, and 3.8 ml of a 5.04% solution of methyllithium in ethyl ether was added dropwise with stirring. The mixture was warmed to room temperature, lithium chloride was removed by filtration, and the filtrate was evaporated in vacuo. The residue was digested with pentane, the mixture was filtered, and the filtrate was evaporated, to give C₅H₅Ta(CH₃)₄ as a yellow oil; yield 1.45 g.

¹H nmr (τ, C₆D₆): 4.78 (5, s); 9.10 (12, s).

A solution of C₅H₅Ta(CH₃)₄ in ethyl ether was prepared as described above from 1.6 g of C₅H₅Ta(CH₃)₃Cl. It was evaporated to about 10 ml in vacuo, a solution of 1.6 g of (C₆H₅)₃C⁺BF₄⁻ in 50 ml of dichloromethane was added, the mixture was stirred for one-half hour, and 0.75 g of 1,2-bis(dimethylphosphino)ethane was added. The volume of the solution was reduced slightly in vacuo, ethyl ether was added, and the solution was cooled at −30° C. The solid that precipitated was separated by filtration to give 2.35 g of [(C₅H₅)[(CH₃)₂PCH₂CH₂P(CH₃)₂]-Ta(CH₃)₃]⁺BF₄⁻ containing a mole of CH₂Cl₂ of crystallization. The latter was removed by pumping at 25° C and 1μ for two hours.

Anal. Calcd for C₁₄H₃₀BF₄P₂Ta: C, 31.84; H, 5.72. Found: C, 31.87; H, 5.56; C, 32.02; H, 5.89; C, 31.92; H, 5.65.

¹H nmr (τ, CD₃CN): 3.74 (5, dd, J = 1.4, .6), 7.58 (4, m), 8.26, 8.40, 8.62, 8.77 (3 each, d, J ≈ 8), 9.75 (3, dd, J = 3.2, 12.0), 10.20 (6, ~t, J≈ 12).

[(C₅H₅)[(CH₃)₂PCH₂CH₂P(CH₃)₂]Ta(CH₃)₃]⁺BF₄⁻·CH₂Cl₂ (0.31 g) in ca. 10 ml of tetrahydrofuran was treated with 0.045 g of (CH₃)₃P=CH₂. All solids dissolved. Workup as in Example 10 gave a pentane solution of C₅H₅[(CH₃)₂PCH₂CH₂P(CH₃)₂]Ta(CH₃)₂=CH₂, which was dissolved in perdeuterobenzene for nmr analysis.

¹H nmr (C₆D₆, τ approximate, J(Hz): 2.2 (2, dd, J = 10, 30), 3.7 (5, d, J = 2), 7.4–8.3 (16, m), 9.1 (3, dd, J = 5, 10), 9.8 (3, dd, J = 12, 15).

The products C₅H₅[(CH₃)₃P]₂Ta(CH₃)₂=CH₂ and C₅H₅[(C₆H₅)₃P]₂Ta(CH₃)₂=CH₂ can be prepared by substituting two moles of trimethylphosphine or triphenylphosphine for each mole of dmpe in essentially the foregoing procedure.

The scope of the organic carbonyl compounds that can be reacted with the products of the invention is quite broad. Operable carbonyl compounds include, but are not limited to, the formula R'—CO—R'' wherein R' is hydrocarbyl and R'' is H, R', OR', or NR'₂. When there are two or three R' groups in a molecule, they can be the same or different. R' and R'' can be aliphatic, cycloaliphatic, or aromatic, and they can be saturated or can contain ethylenic or acetylenic unsaturation. In addition, R' and R'' can be joined together to form a divalent group. R and R' can contain halo, hydrocarbyloxy, hydrocarbylthio, and/or dihydrocarbylamino substituents. The number of carbons in the R' and R'' groups is not critical and is limited only by availability. Preferably, any one R' or R'' group will contain at most 18 carbons, and more preferably it will contain at most 12 carbons.

EXAMPLE A

To a solution of a small quantity of $(C_5H_{11})_3Ta=C_5H_{10}$ in about five times its weight of pentane was added a solution of an equimolar amount of acetone and about three volumes of pentane. The orange color of the tantalum compound immediately disappeared, and a mixture of a pale-yellow liquid and a pale-yellow solid resulted. The solid was separated by filtration, and the filtrate was distilled under reduced pressure. The distillate was a mixture of pentane and 2,4,4-trimethyl-2-pentene. The latter was identified by mass spectroscopy and by comparison with an authentic sample.

EXAMPLE B

By essentially the method of Example A, $(C_5H_{11})_3Ta=C_5H_{10}$ was reacted with an equivalent amount of cyclohexanone. The filtrate was analyzed directly, without distillation, by gas chromatography and mass spectroscopy, and shown to contain neopentylidenecyclohexane. The product was identified by mass spectroscopy and by its $^1H$ nmr after isolation by preparative gas chromatography. $^1H$ nmr (CDCl$_3$): τ4.83 (m, 1), τ7.5–8.7 (m, 10), τ8.90 (s, 9).

EXAMPLE C

By essentially the method of Example A, $(C_5H_{11})_3Ta=C_5H_{10}$ was reacted with an equivalent amount of 3-methylacetophenone. After removal of the pentane under reduced pressure, there remained a 3:1 mixture of the cis and trans isomers of 4,4-dimethyl-2-(m-tolyl)-2-pentene. The products were identified by mass spectroscopy and by $^1H$ nmr (in CDCl$_3$: one isomer at τ2.7–2.8 (m, 4), τ4.55 (q, 1), τ7.66 (s, 3), τ8.06 (d, 3) and τ9.14 (s, 9); the other isomer at τ2.7–2.8, τ4.27, τ7.67, τ7.89, and τ8.80).

EXAMPLE D

By essentially the method of Example C, $(C_5H_{11})_3Ta=C_5H_{10}$ was reacted with benzaldehyde to give an approximately 2:1 mixture of the cis and trans isomers of 3,3-dimethyl-1-phenyl-1-butene, which were identified by mass spectroscopy.

EXAMPLE E

Equivalent amounts of $(C_5H_{11})_3Ta=C_5H_{10}$ and ethyl acetate were dissolved in pentane, and the solution was stirred for 1.5 hr at room temperature. The pale-yellow solid that had precipitated was removed by filtration, and the filtrate was shown by mass spectroscopy to contain a mixture of the cis and trans isomers of 2-ethoxy-4,4-dimethyl-2-pentene.

EXAMPLE F

A mixture of 0.34 g of $(C_5H_5)_2Ta(CH_3)=CH_2$ and 2 ml of cyclohexanone was warmed to about 90° C for five minutes four times over a period of six hours. All volatile materials were distilled into a trap under reduced pressure. Methylenecyclohexane was identified in the volatile material by gas chromatography and mass spectrometry.

The products of the invention also react with molecular oxygen to give symmetrical ethylenically unsaturated hydrocarbons. The following is illustrative.

EXAMPLE G

A solution of $(C_5H_{11})_3Ta=C_5H_{10}$ in pentane was stirred under an atmosphere of oxygen at room temperature for two days. Analysis of the resulting solution by gas chromatography and mass spectroscopy showed that 2,2,5,5-tetramethyl-3-hexene had been formed.

The products of the invention, because of their sensitivity to oxygen, are useful for removing small amounts of oxygen from gases and mixtures of gases. For this purpose, the product can be used as obtained from a reaction mixture, or more preferably, in solution in an inert solvent. In addition, a product can be deposited on an inert support from a solution in an inert solvent. After removal of traces of solvent by evaporation, the product-coated support can be used for trapping oxygen.

EXAMPLE H

Oxygen was bubbled through a solution of about 0.2 g of $(C_5H_5)_2Ta(CH_3)=CH_2$ in 1 ml of dichlorodideuteromethane. A rapid reaction occurred, with about half the tantalum compound being reacted with the oxygen in one minute, as determined by changes in the nmr spectrum.

EXAMPLE I

When oxygen was bubbled through a solution of $(C_5H_{11})_3Ta=C_5H_{10}$ in dichloromethane at room temperature, the characteristic orange color of the product in solution changed to a pale yellow in less than 1 min, indicating a rapid reaction of oxygen with the product.

The products of this invention decompose thermally on heating the vapor at temperatures above about 500° C with the deposition of metallic tantalum or niobium, and thus can be employed to form mirrors on glass or other substrates.

EXAMPLE J

A sample of $(C_5H_{11})_3Ta=C_5H_{10}$ was volatilized under high vacuum in a glass vessel, different parts of which were heated to different temperatures. Where the temperature of the interior glass surface was about 600° C, a mirror of tantalum metal formed on said surface when the vapor came in contact with it.

In addition, the products are useful as catalysts for isomerization and hydrogenation of olefins. For example, $(C_5H_{11})_3Ta=C_5H_{10}$ catalyzes the hydrogenation of 1-butene in solution at 25° C and 30 psi.

The products of the invention also react with alkyllithium compounds such as methyllithium and butyllithium, in the presence of donor solvents, to give solvated lithium derivatives in which a hydrogen on the carbon doubly bonded to tantalum has been replaced by lithium. For example, $(C_5H_{11})_3Ta=CHC(CH_3)_3$ reacts with methyllithium in the presence of tetrahydrofuran to give a product of the formula $(C_5H_{11})_3TaC[Li(C_4H_8O)_2]C(CH_3)_3$. Other donor molecules that can be used include dioxane, N,N,N',N'-tetramethylethylenediamine, and N,N'-dimethylpiperazine.

I claim:
1. A compound having the formula

$$Cp_aL_bQ_cM=CR^1R^2$$
$$|$$
$$X$$

wherein

Cp is π-cyclopentadienyl having up to one alkyl substituent;

L is $P(R^3)_3$ or $(R^3)_2PCH_2CH_2P(R^3)_2$ in which $R^3$ is alkyl or aryl;

Q is alkyl, aralkyl or diarylmethyl in which the β-carbon is not bonded to hydrogen;

M is niobium or tantalum;

X is F, Cl, Br, I or alkyl, aralkyl or diarylmethyl in which the β-carbon is not bonded to hydrogen;

$R^1$ and $R^2$ individually are hydrogen, tertiary alkyl or aryl, only one of $R^1$ and $R^2$ being tertiary alkyl;

alkyl has 1–10 carbons, aralkyl has 7–10 carbons and aryl, including the aryl groups in diarylmethyl, has 6–10 carbons;

$a$, $b$ and $c$ individually are 0, 1 or 2;

with the proviso that $b$ is 1 when L is a diphosphine or 2 when L is a monophosphine; and with the further provisos that when $a$ is 2, $b$ and $c$ are each 0;

when $a$ is 1, $b$ is 1 or 2, $c$ is 1, Q and X are each $CH_3$ and $R^1$ and $R^2$ are each H; and when $a$ is 0, $b$ is 0, $c$ is 2 and X is the same as Q.

2. A compound of claim 1 where $a$ is 2 and $b = c = 0$.

3. A compound of claim 1 where $a$ is 1, $b$ is 1 or 2, $c$ is 1, Q and X are each $CH_3$ and $R^1$ and $R^2$ are each H.

4. A compound of claim 1 where $a = b = 0$, $c$ is 2 and X is the same as Q.

5. A compound of claim 1 where M is niobium.

6. A compound of claim 1 where M is tantalum.

7. The compound of claim 1 which is trineopentyl(neopentylidene)tantalum.

8. The compound of claim 1 which is trineopentyl(neopentylidene)niobium.

9. The compound of claim 1 which is dicyclopentadienyl(methyl)(methylene)tantalum.

10. The compound of claim 1 which is 1,2-bis(dimethylphosphino)ethane(π-cyclopentadienyl)(dimethyl)-(methylene)tantalum.

* * * * *